United States Patent [19]

Sieber et al.

[11] Patent Number: 5,324,833
[45] Date of Patent: Jun. 28, 1994

[54] PROTECTED AMINO ACIDS AND PROCESS FOR THE PREPARATION THEREOF

[75] Inventors: Peter Sieber, Reinach; Bernhard Riniker, Frenkendorf, both of Switzerland

[73] Assignee: Novabiochem AG, Laufelfingen, Switzerland

[21] Appl. No.: 509,102

[22] Filed: Apr. 13, 1990

[30] Foreign Application Priority Data

Apr. 17, 1989 [CH] Switzerland .................. 1439/89
Jun. 20, 1989 [CH] Switzerland .................. 2300/89

[51] Int. Cl.$^5$ .................. C07D 253/04; C07D 487/04; C07C 229/24
[52] U.S. Cl. ..................... 544/183; 552/104; 548/256; 548/262.4; 560/39; 560/41; 562/441
[58] Field of Search .................. 548/256, 262.4; 544/182; 560/39, 41; 562/441; 552/104

[56] References Cited

U.S. PATENT DOCUMENTS

4,871,870  10/1989  Kim ................................ 560/39

FOREIGN PATENT DOCUMENTS

292228  11/1988  European Pat. Off. .
1065424  9/1959  Fed. Rep. of Germany .
1768047  11/1971  Fed. Rep. of Germany .

OTHER PUBLICATIONS

K. Okawa et al., Chem. Abstract, vol. 93, p. 26820, Abst. No. 93:26813n. (1960).
S. Wang et al., "Facile Synthesis of Amino Acid and Peptide Esters under Mild Conditions via Cesium Salts", *J. Org. Chem.*, vol. 42, No. 8, 1977, pp. 1286-1290.
Sieber and Riniker, copy of poster at Symposium on Solid Phase Synthesis in Oxford UK, on Aug. 29-Sep. 2, 1989.
Houben-Weyl, "Methoden der Organischen Chemie," 4th ed. vol. XV/1, Stuttgart 1974 pp. 711-727.
Sieber, et al. Tetrahedron Letters 28(1987) 6031-6034.
Weygand, et al. Chem. Ber 101(1968) 3642-3648.
Pietta, et al. Chem. Ber 101(1968) 3649-3651.
Konig, et al. Chem Ber 103(1970) 2041-2051.
Weygand et al. Chem. Ber. 101(1968) 3623-3641.

*Primary Examiner*—Robert W. Ramsuer
*Assistant Examiner*—Jacqueline Haley
*Attorney, Agent, or Firm*—Seidel, Gonda, Lavorgna & Monaco

[57] ABSTRACT

Compounds of the formula I,

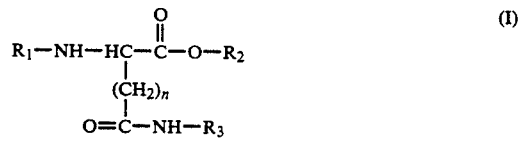

in which 'R$_1$ is an amino protective group, and n stands for 1 or 2, R$_1$ denotes hydrogen or an amino protective group, R$_2$ denotes hydrogen or a carboxyl protective group and R$_3$ denotes triphenylmethyl, 4-monomethoxy-trityl or 4,4'-dimethoxy-trityl, and reactive carboxylic acid derivatives of such compounds of the formula I in which R$_2$ stands for hydrogen, are described.

These compounds can be used as starting materials for the preparation of peptides. They are more suitable for this than are analogous compounds of the formula I in which R$_3$ denotes hydrogen or one of the carbamoyl protective groups hitherto customary.

20 Claims, 1 Drawing Sheet

FIG. 1A           FIG. 1B

PROTECTED AMINO ACIDS AND PROCESS FOR THE PREPARATION THEREOF

The invention relates to amino acid derivatives containing N-trityl-carbamoyl groups, process for the preparation thereof, and the use thereof in peptide synthesis.

The amide groups of the amino acids asparagine and glutamine often lead to undesired side reactions in peptide synthesis, for example dehydration to the nitrile, intramolecular cyclization to the imide and, in the case of glutamine, to pyrrolidone formation. In addition, it is often observed in solid-phase synthesis with glutamine that the peptide-resins no longer swell, because of intermolecular formation of hydrogen bonds, which results in poor coupling yields.

These disadvantages can be avoided by protecting the carbamoyl groups of asparagine and glutamine. Commonly used as protective group is 4,4'-dimethoxy-diphenyl-methyl (di-[4-methoxy-phenyl]-methyl, 4,4'-dimethoxy-benzhydryl, abbreviation: Mbh) or 2,4,6-trimethoxy-benzyl (abbreviation: Tmob).

However, the inventors of the present invention have now found that in certain cases the carbamoyl protective groups hitherto known themselves cause undesired side reactions when they are eliminated. This is because the carbocations formed in the acidolytic elimination react very readily and in an irreversible manner with tryptophan.

Starting from this finding which, as its starting point, is to a certain extent part of the present invention, the object of the present invention was now to find a carbamoyl protective group with which the said side reactions do not occur and to prepare correspondingly protected amino acid derivatives.

The invention relates to compounds of the formula I in which n stands for 1 or 2, $R_1$ denotes hydrogen or an amino protective group, $R_2$ denotes hydrogen or a carboxyl protective group and $R_3$ denotes triphenylmethyl, 4-monomethoxy-trityl or 4,4'-dimethoxy-trityl, salts of those compounds which have a salt-forming group and reactive carboxylic acid derivatives of those compounds of the formula I in which $R_1$ is an amino protective group, and $R_2$ stands for hydrogen. The configuration at the asymmetric HC atom is (D,L), (D) or, preferably, (L).

In peptide synthesis, the compounds of the formula I have no alkylating action on the indole side-chain of tryptophan. In addition, they are more easily obtained, more soluble in organic solvents, and their amide protective group can be eliminated more easily with trifluoroacetic acid than in analogous compounds in which $R_3$ stands for 2,4,6-trimethoxy-benzyl (Tmob) or di-(4-methoxy-phenyl)-methyl (Mbh). For example, the half-lives of Fmoc-Gln(Trt)-OH, Fmoc-Gln(Tmob)-OH and Fmoc-(Gln(Mbh)-OH on cleavage in trifluoroacetic acid/1,2-dichloroethane (1:1) at 22° C. are 2, 9 and 27 minutes respectively.

The reactive carboxylic acid derivatives of the compounds of the formula I are, under coupling conditions, that is to say in the presence of coupling catalysts such as 1-hydroxy-1H-benzotriazole (HOBt), and in the presence of solvents which are customarily used for coupling reactions in peptide synthesis, for example dimethylacetamide (DMA) and 1,2-dichloro-ethane (DIEA), distinctly more stable than analogous compounds in which $R_3$ denotes hydrogen. For example, the decomposition half-lives of Fmoc-Asn-O-Tcp and Fmoc-Asn-O-Pfp (Fmoc=9-fluorenyl-methoxy-carbonyl, Pfp=pentafluoro-phenyl, Tcp=2,4,5-trichloro-phenyl) in DMA+1 equivalent of HOBt+1.7 equivalents of DIEA are only 2 minutes and even less than 1 minute, respectively, whereas the analogous compounds in which $R_3$ denotes a trityl radical are completely stable under the same conditions.

Surprisingly, the space-filling trityl protective groups do not slow down the coupling reactions, on the contrary they have virtually no effect on the rate of coupling.

Protective groups, the introduction and elimination thereof are described, for example, in "Protective Groups in Organic Chemistry", Plenum Press, London, New York 1973, and in "Methoden der organischen Chemie" (Methods of Organic Chemistry), Houben-Weyl, 4th edition, Vol. 15/1, Georg-Thieme-Verlag, Stuttgart 1974 and in Theodora W. Greene, "Protective Groups in Organic Synthesis", John Wiley & Sons, New York 1981. It is characteristic of protective groups that they can be eliminated easily, that is to say without undesired side reactions taking place, for example by solvolysis, reduction, photolysis or else under physiological conditions.

A protected amino group $R_1$-NH can be in the form of, for example, an easily cleavable acylamino, arylmethylamino, etherified mercaptoamino, 2-acyl-lower-alk-1-enyl-amino or silyl-amino group.

Acyl in a corresponding acylamino group is, for example, the acyl radical of an organic carboxylic acid with, for example, up to 18 carbon atoms, in particular of an alkanecarboxylic acid which is optionally substituted, for example by halogen or aryl, or benzoic acid which is optionally substituted, for example by halogen, lower alkoxy or nitro, or of a monoester of carbonic acid. Examples of such acyl groups are lower alkanoyl such as formyl, acetyl or propionyl, halogeno-lower-alkanoyl such as 2-halogenoacetyl, in particular 2-chloro-, 2-bromo-, 2-iodo-, 2,2,2-trifluoro- or 2,2,2-trichloroacetyl, benzoyl which is optionally substituted, for example by halogen, lower alkoxy or nitro, for example benzoyl, 4-chlorobenzoyl, 4-methoxybenzoyl or 4-nitrobenzoyl, or lower alkoxycarbonyl which is branched in the 1 position of the lower alkyl radical or suitably substituted in the 1 or 2 position, in particular tert.-lower-alkoxycarbonyl, for example tert.-butyloxycarbonyl, arylmethoxycarbonyl with one or two aryl radical which preferably represent phenyl which is optionally mono- or polysubstituted, for example by lower alkyl, in particular tert.-lower-alkyl such as tert.-butyl, lower alkoxy such as methoxy, hydroxy, halogen, for example chlorine, and/or nitro, such as optionally substituted benzyloxycarbonyl, for example 4-nitrobenzyloxycarbonyl, or substituted diphenylmethoxycarbonyl, for example benzhydryloxycarbonyl or di-(4-methoxyphenyl)-methoxycarbonyl, aroylmethoxycarbonyl in which the aroyl group preferably represents benzoyl which is optionally substituted, for example by halogen such as bromine, for example phenacyloxycarbonyl, 2-halogeno-lower-alkoxycarbonyl, for example 2,2,2-trichloroethoxycarbonyl, 2-bromoethoxycarbonyl or 2-iodoethoxycarbonyl, or 2-(trisubstituted silyl)-ethoxycarbonyl in which the substituents each, independently of one another, denote an optionally substituted (for example substituted by lower alkyl, lower alkoxy, aryl, halogen or nitro) aliphatic, araliphatic, cycloaliphatic or aromatic hydrocarbon radical with up to 15 C atoms, such as appropriate optionally substituted lower alkyl, phenyl-lower-alkyl, cycloalkyl or phenyl, for example 2-tri-lower-alkylsilylethoxycarbonyl such as 2-trimethylsilylethoxycarbonyl or 2-(di-n-butyl-methylsilyl)-ethoxycarbonyl, or 2-triarylsilylethoxycarbonyl such as 2-triphenylsilylethoxycarbonyl.

Other acyl radicals suitable as amino protective groups $R_1$ are also appropriate radicals of organic phosphoric, phosphonic or phosphinic acids such as di-lower-alkylphosphoryl, for example dimethylphosphoryl, diethylphosphoryl, di-n-propylphosphoryl or diisopropylphosphoryl, dicycloalkylphosphoryl, for example dicyclohexylphosphoryl, optionally substituted diphenylphosphoryl, for example diphenylphosphoryl, optionally substituted, for example by nitro, di-(phenyl-lower-alkyl)-phosphoryl, for example dibenzylphosphoryl or di-(4-nitrobenzyl)-phosphoryl, optionally substituted phenyloxyphenylphosphonyl, for example phenyloxyphenyl-phosphonyl, di-lower-alkylphosphonyl, for example diethylphosphinyl, or optionally substituted diphenylphosphinyl, for example diphenylphosphinyl.

The aryl radicals in an arylmethylamino group, which represents a mono-, di- or, in particular, triarylmethylamino group, are, in particular, optionally substituted phenyl radicals. Examples of such groups are benzyl-, diphenylmethyl- and, in particular, tritylamino.

An etherified mercapto group in an amino group protected with a radical of this type is primarily arylthio or aryl-lower-alkylthio in which aryl is, in particular, phenyl which is optionally substituted for example by lower alkyl such as methyl or tert.-butyl, lower alkoxy such as methoxy, halogen such as chlorine, and/or nitro. An example of an appropriate amino protective group is 2-nitrophenylthio.

Acyl in a 2-acyl-lower-alk-1-en-1-yl radical which can be used as an amino protective group is, for example, the appropriate radical of a lower alkanecarboxylic acid, of a benzoic acid which is optionally substituted, for example by lower alkyl such as methyl or tert.-butyl, lower alkoxy such as methoxy, halogen such as chlorine, and/or nitro or, in particular, of a monoester of carbonic acid, such as of a mono-lower-alkyl ester of carbonic acid. Appropriate protective groups are primarily 1-lower-alkanoyl-prop-1-en-2-yl, for example 1-acetyl-prop-1-en-2-yl, or 1-lower-alkoxycarbonyl-prop-1-en-2-yl, for example 1-ethoxycarbonyl-prop-1-en-2-yl.

Preferred amino protective groups are acyl radicals of monoesters of carbonic acid, in particular tert.-butyloxycarbonyl, benzyloxycarbonyl which is optionally substituted, for example as stated, for example 4-nitro-benzyloxycarbonyl, or diphenylmethoxycarbonyl, or 2-halogeno-lower-alkoxycarbonyl such as 2,2,2-trichloroethoxycarbonyl, or allyloxycarbonyl and protective groups related to the latter, or, especially, 9-fluorenyl-methoxycarbonyl.

Carboxyl protective groups $R_2$ are normally esterifying groups, primarily lower alkyl groups which are branched in the 1 position or suitably substituted in the 1 or 2 position. Preferred carboxyl groups in the esterified form are, inter alia, tert.-lower-alkoxycarbonyl, for example tert.-butyloxycarbonyl, arylmethoxycarbonyl with one or two aryl radicals, the latter representing phenyl radicals which are optionally mono- or polysubstituted, for example by lower alkyl such as tert.-lower-alkyl, for example tert.-butyl, lower alkoxy such as methoxy, hydroxy, halogen, for example chlorine, and/or nitro, such as benzyloxycarbonyl which is optionally substituted, for example as mentioned above, for example 4-methoxybenzyloxycarbonyl or 4-nitrobenzyloxycarbonyl, or diphenyl-methoxycarbonyl which is optionally substituted, for example as mentioned above, for example diphenylmethoxycarbonyl or di-(4-methoxyphenyl)-methoxycarbonyl, 1-lower-alkoxy-lower-alkoxycarbonyl such as methoxymethoxycarbonyl, 1-methoxyethoxy-carbonyl or 1-ethoxymethoxycarbonyl, 1-lower-alkylthio-lower-alkoxycarbonyl such as 1-methylthiomethoxycarbonyl or 1-ethylthioethoxycarbonyl, aroylmethoxycarbonyl in which the aroyl group represents benzoyl which is optionally substituted, for example by halogen such as bromine, for example phenacyloxycarbonyl, 2-halogeno-lower-alkoxycarbonyl, for example 2,2,2-trichloroethoxycarbonyl, 2-bromoethoxycarbonyl or 2-iodoethoxycarbonyl or 2-(trisubstituted silyl)-ethoxycarbonyl in which the substituents each, independently of one another, denote an optionally substituted (for example substituted by lower alkyl, lower alkoxy, aryl, halogen, and/or nitro) aliphatic, araliphatic, cycloaliphatic or aromatic hydrocarbon radical such as appropriate, optionally substituted lower alkyl, phenyl-lower-alkyl, cycloalkyl or phenyl, for example 2-tri-lower-alkylsilyl-ethoxycarbonyl, 2-trimethylsilylethoxycarbonyl or 2-(di-n-butyl-methylsilyl)-ethoxycarbonyl, or 2-triarylsilylethoxycarbonyl such as 2-triphenylsilylethoxycarbonyl.

Preferred protected carboxyl groups are tert.-lower-alkoxycarbonyl such as tert.-butoxycarbonyl and, primarily, benzyloxycarbonyl which is optionally substituted, for example as mentioned above, such as 4-nitrobenzyloxycarbonyl, or diphenylmethoxycarbonyl, and especially 2-(trimethylsilyl)-ethoxycarbonyl.

A salt-forming group in a compound of the formula I is, for example, a free amino group ($R_1$=H) or a free carboxyl group ($R_2$=H). The compounds of the formula I in which $R_1$ denotes hydrogen can form acid addition salts, for example with inorganic acids such as hydrochloric acid, sulfuric acid or phosphoric acid, or with suitable organic carboxylic or sulfonic acids, for example trifluoroacetic acid. The compounds of the formula I in which $R_2$ denotes hydrogen can form metal or ammonium salts, for example alkali metal or alkaline earth metal salts, for example sodium, potassium, magnesium or calcium salts, or salts with ammonia or suitable organic amines, primarily suitable for the salt formation being aliphatic, cycloaliphatic, cycloaliphatic-aliphatic or araliphatic primary, secondary or tertiary mono-, di- or polyamines, as well as heterocyclic bases, such as lower alkylamines, for example triethylamine, hydroxy-lower-alkylamines, for example 2-hydroxyethylamine, bis-(2-hydroxyethyl)-amine, 2-hydroxyethyl-diethyl-amine or tri-(2-hydroxyethyl)-amine, basic aliphatic esters of carboxylic acids, for example 2-diethylaminoethyl 4-amino-benzoate, lower alkyleneamines, for example 1-ethylpiperidine, cycloalkylamines, for example dicyclohexylamine, or benzylamines, for example N,N'-dibenzylethylenediamine, furthermore bases of the pyridine type, for example pyridine, collidine or quinoline.

Compounds of the formula I in which $R_1$ and $R_2$ denote hydrogen can form inner salts.

These salts can be used, inter alia, for the isolation or purification of the compounds of the formula I in which $R_1$ and/or $R_2$ denote hydrogen.

Reactive carboxylic acid derivatives of a compound of the formula I in which $R_1$ is an amino protective group, and $R_2$ stands for hydrogen are primarily reactive activated esters or reactive anhydrides, furthermore reactive cyclic amides.

Activated esters of acids are, in particular, esters which are unsaturated at the linkage carbon atom of the esterifying radical, for example of the vinyl ester type, such as actual vinyl esters (which can be obtained, for example, by transesterification of an appropriate ester with vinyl acetate; activated vinyl ester method), carbamoylvinyl esters (which can be obtained, for example, by treatment of the appropriate acid with an isoxazolium reagent; 1,2-oxazolium or Woodward method), or 1-lower-alkoxyvinyl esters (which can be obtained, for example, by treatment of the appropriate acid with a lower alkoxyacetylene; ethoxyacetylene method), or esters of the amidino type such as N,N'-disubstituted amidino esters (which can be obtained, for example, by treatment of the appropriate acid with a suitable N,N'-disubstituted carbodiimide, for example N,N'-dicyclohexylcarbodiimide; carbodiimide method), or N,N-disubstituted amidino esters (which can be obtained, for example, by treatment of the appropriate acid with an N,N-disubstituted cyanamide; cyanamide method), suitable aryl esters, in particular phenyl esters suitably substituted, in particular, by electron-attracting substituents (which can be obtained, for example, by treatment of the appropriate acid with a suitably substituted phenol, for example 4-nitrophenol, 4-methylsulfonylphenol, 2,4,5-trichlorophenol, 2,3,4,5,6-pentachlorophenol, 2,3,4,5,6-pentafluorophenol or 4-phenyldiazophenol, in the presence of a condensing agent such as N,N'-dicyclohexyl-carbodiimide; activated aryl ester method), cyanomethyl esters (which can be obtained, for example, by treatment of the appropriate acid with chloroacetonitrile in the presence of a base; cyanomethyl ester method), thioesters, in particular phenyl thioesters which are optionally substituted, for example by nitro (which can be obtained, for example, by treatment of the appropriate acid with thiophenols which are optionally susbtituted, for example by nitro, inter alia by means of the anhydride or carbodiimide method; activated thiol ester method), amino or amido esters (which can be obtained, for example, by treatment of the appropriate acid with an N-hydroxy-amino or N-hydroxy-amido compound, for example N-hydroxy-succinimide, N-hydroxy-5-norbornene-2,3-dicarboximide, N-hydroxy-piperidine, N-hydroxy-phthalimide, 1-hydroxy-benzotriazole or 3,4-dihydro-3-hydroxy-4-oxo-1,2,3-benzotriazine, for example by the anhydride or carbodiimide method; activated N-hydroxy ester method), or silyl esters (which can be obtained, for example, by treatment of the appropriate acid with a silylating agent, for example hexamethyldisilazane, and which react readily with hydroxyl but not with amino groups).

Anhydrides of acids can be symmetric or, preferably, mixed anhydrides of these acids, thus, for example, anhydrides with inorganic acids, such as acid halides, in particular acid chlorides (which can be obtained, for example, by treatment of the appropriate acid with thionyl chloride, phosphorous pentachloride or oxalyl chloride; acid chloride method), azides (which can be obtained, for example, from an ester of an appropriate acid via the corresponding hydrazide and treatment thereof with nitrous acid; azide method), anhydrides with mono derivatives of carbonic acid, such as with appropriate esters, for example mono-lower-alkyl esters of carbonic acid (which can be obtained, for example, by treatment of the corresponding acid with lower alkyl halogeno-, such as chloroformates, or with a 1-loweralkoxycarbonyl-2-lower-alkoxy-1,2-dihydro-quinoline, for example 1-lower-alkoxycarbonyl-2-ethoxy-1,2-dihydroquinoline; mixed O-alkyl carbonic anhydride method), or anhydrides with dihalogenated, in particular dichlorinated, phosphoric acid (which can be obtained, for example, by treatment of the corresponding acid with phosphorus oxychloride; phosphorus oxychloride method), or anhydrides with organic acids, such as mixed anhydrides with organic carboxylic acids (which can be obtained, for example, by treatment of the appropriate acid with an optionally substituted lower alkane- or phenylalkanecarbonyl halide, for example phenylacetyl, pivaloyl or trifluoroacetyl chloride; mixed carboxylic anhydride method), or with organic sulfonic acids (which can be obtained, for example, by treatment of a salt, such as an alkali metal salt, of the appropriate acid with a suitable organic sulfonyl halide such as lower alkane-or aryl-, for example methane- or p-toluenesulfonyl chloride; mixed sulfonic anhydride method), as well as symmetric anhydrides (which can be obtained, for example, by condensation of the appropriate acid in the presence of a carbodiimide or of 1-diethylaminopropyne; symmetric anhydride method).

Suitable cyclic amides are, in particular, amides with five-membered diazacycles which are aromatic in nature, such as amides with imidazoles, for example imidazole (which can be obtained, for example, by treatment of the appropriate acid with N,N'-carbonyldiimidazole; imidazolide method), or pyrazoles, for example 3,5-dimethyl-pyrazole (which can be obtained, for example, via the acid hydrazide by treatment with acetylacetone; pyrazolide method).

The abbreviations used for the amino acids in this text are those generally customary. Thus, Asp denotes aspartic acid, Asn denotes asparagine, Gln denotes glutamine, Ser denotes serine, Leu denotes leucine, Gly denotes glycine, Lys denotes lysine, His denotes histidine, Pro denotes proline, Tyr denotes tyrosine, Trp denotes tryptophan, Arg denotes arginine, Val denotes valine and Ile denotes isoleucine.

In conformity with the internationally recognized rules of nomenclature, the abbreviations in this text for the amino acids, for example the abovementioned abbreviations, designate the free acid and, unless stated otherwise, the L configuration. The $\alpha$-amino group is to be thought of as being on the left-hand side of the abbreviation, and the carboxyl group on the right-hand side.

The absence of an H atom in the α-amino group is indicated by a dash on the left of the abbreviation for the amino acid, and the absence of two H atoms is indicated by two dashes on the left. The absence of an HO group in the carboxyl group is indicated by a dash on the right. Substituents in the side-chain of amino acids are placed in parentheses immediately after the amino acid symbol. Thus, for example, Z-Asn(Trt)-OH stands for the compound of the formula Ia.

The advantages achieved by use of the compounds of the formula I in peptide synthesis are illustrated in the Examples section. Thus, for example, H-Gln-Gln-Gln-Gln-Gln-Ser-Leu-Gly-OH is obtained as crude product in a purity of 92% when the carbamoyl group of the Gln residues is protected by trityl during the preparation. Without this protection during the Merrifield synthesis, the crude product contains only 30% of the desired product, not 92% as above.

The crude products obtained from the syntheses of Fmoc-Lys-Gln-His-Asn-Pro-Lys-Tyr-Gln-Trp-Asn-OH with trityl protection of the carbamoyl groups of Asn and Gln (crude product A) on the one hand and with 2,4,6-trimethoxy-benzyl protection (crude product B) on the other hand have about 95% of the desired product in crude product A and only about 8% of the desired product in crude product B.

The compounds of the formula I can be used as building blocks in the synthesis of any desired peptides which contain glutamine and/or asparagine residues or as intermediates for the preparation of these building blocks. Used for Merrifield peptide synthesis are those compounds of the formula I in which $R_1$ denotes an amino protective group such as, in particular, 9-fluorenylmethoxycarbonyl or tert.-butyloxycarbonyl, $R_2$ denotes hydrogen and $R_3$ denotes triphenylmethyl, 4-monomethoxy-trityl or 4,4'-dimethoxy-trityl, and reactive carboxylic acid derivatives thereof.

Preferred compounds of the formula I are those in which $R_1$ denotes benzyloxycarbonyl, 9-fluorenylmethoxycarbonyl, allyloxycarbonyl or tert.-butyloxycarbonyl, $R_2$ denotes hydrogen and $R_3$ denotes triphenylmethyl.

Particularly preferred compounds of the formula I are those described in the Examples.

Of the reactive carboxylic acid derivatives described in detail above, particularly worthy of mention are the 2,4,5-trichloro-phenyl esters, the pentafluoro-phenyl esters, the esters with 1-hydroxybenzotriazole, with 3,4-dihydro-3-hydroxy-4-oxo-1,2,3-benzotriazine or with N-hydroxy-5-norbornene-2,3-dicarboximide, the acid chlorides and the symmetric anhydrides, especially those reactive carboxylic acid derivatives of the compounds of the formula I pointed out above as preferred.

Surprisingly, the amide protective group $R_3$ according to the invention is stable during the catalytic hydrogenation under conditions under which benzyloxycarbonyl or $R_3$ as amino protective groups or benzyl as carboxyl protective group are already eliminated. The protective group $R_3$ can be eliminated, for example, with trifluoroacetic acid/water/1,2-ethanedithiol (90:5:5) in the temperature range between room temperature and +50° C., for example at +30° C.

The compounds of the formula I are prepared in a manner known per se. The preparation process according to the invention is characterized in that a) a compound of the formula II in which $R_4$ stands for hydrogen or an amino protective group which is stable under the reaction conditions, and n and $R_2$ have the abovementioned meanings, is reacted with a compound of the formula III in which $R_3$ has the abovementioned meaning, and those protective groups which do not form part of the desired final product of the formula I are eliminated from the resulting product, or b) for the preparation of a compound of the formula I in which $R_1$ stands for an amino protective group, an amino protective group is introduced into a compound of the formula IV in which n, $R_2$ and $R_3$ have the abovementioned meanings, or c) a compound of the formula V in which n has the abovementioned meaning, $R_5$ denotes an amino protective group which is stable under the reaction conditions, and $R_6$ stands for a carboxyl protective group which is stable under the reaction conditions, is reacted with a compound of the formula VI in which $R_3$ has the abovementioned meaning, and those protective groups which do not form part of the desired final product of the formula I are eliminated from the resulting product, and, if desired, after one of the processes a), b) or c) has been carried out, a resulting compound of the formula I with a salt-forming group is converted into its salt, or a resulting salt is converted into the free compound, or a resulting compound of the formula I in which $R_1$ is an amino protective group, and $R_2$ denotes hydrogen is converted into a reactive carboxylic acid derivative.

The abovementioned process variants are explained in detail hereinafter:

Process a)

Process a) is carried out in a suitable organic solvent such as, for example, acetic acid, in the presence of catalytic amounts of anhydrous strong Lewis acids such as, for example, boron trifluoride, trifluoromethanesulfonic acid or, preferably, sulfuric acid, and in the presence of a dehydrating agent such as, for example, acetic anhydride, in the temperature range between about 0° C. and +100° C., preferably between room temperature (about 20° C.) and +70° C., for example at +50° C. When $R_4$ denotes hydrogen, it is expedient to use more anhydrous sulfuric acid than in the case where $R_4$ denotes an amino protective group, for example 1.1 equivalents, and the reaction is preferably carried out at about +60° C., especially when $R_4$ stands for hydrogen and n stands for 1 in the starting compounds of the formula II.

An amino protective group $R_4$ is an amino protective group which is stable under acid conditions, such as, for example, allyloxycarbonyl, trifluoroacetyl or, preferably, benzyloxycarbonyl or 9-fluorenyl-methoxycarbonyl.

When $R_1$ and/or $R_2$ stand for hydrogen in the desired final product of the formula I it is necessary to eliminate the protective groups $R_4$ and/or $R_2$.

Most carboxyl protective groups $R_2$ are already eliminated under the reaction conditions. The only stable carboxyl protective groups $R_2$ are such as methyl, ethyl or allyl, which can be eliminated, for example, by base-catalysed hydrolysis.

Trifluoroacetyl as amino protective group $R_4$ is eliminated by mild alkaline hydrolysis, for example with aqueous ammonia solution, sodium or barium hydroxide or with basic ion exchanger resins.

Benzyloxycarbonyl as amino protective group $R_4$ is eliminated by hydrogenation in the presence of a palladium on charcoal catalyst in aqueous methanolic hydrochloric acid solution at room temperature and under atmospheric pressure.

9-Fluorenyl-methoxycarbonyl as amino protective group $R_4$ is eliminated using piperidine/dimethylacetamide (1:4) at room temperature. The yields in process a) are about 60-95% of theory.

Process b)

Process b) is carried out in a suitable, optionally aqueous, organic solvent or solvent mixture in the temperature range between about 0° C. and +80° C., preferably at room temperature to +50° C., it also being possible to work in suspension. Thus, for example, 9-fluorenyl-methoxycarbonyl can be introduced as amino protective group $R_1$ by reacting a starting compound of the formula IV in an organic solvent such as tetrahydrofuran or dioxane, in the presence of water and of an inorganic base, such as sodium bicarbonate or sodium hydroxide, and, if necessary, of a tertiary organic amine such as triethylamine, with 9-fluorenylmethyl N-succinimidyl carbonate. Tert.-butyloxycarbonyl as amino protective group $R_1$ can be introduced, for example, in 90% strength aqueous tetrahydrofuran in the presence of triethylamine at room temperature with equimolar amounts of di-tert.-butyl dicarbonate. The yields in process b) are about 90-99% of theory.

In contradistinction to process a), process b) allows any desired amino protective groups $R_1$ to be introduced.

Process c)

Process c) is carried out in a suitable organic solvent such as 1,2-dichloroethane, in the temperature range between −20° C. and +70° C., for example at 0° C., and preferably under a protective gas, for example under argon atmosphere. Necessary for this is an in situ activation of the free carboxyl group in the starting material of the formula V, for example with the aid of 1-chloro-N,N,2-trimethyl-prop-1-enylamine. The yields in process c) are about 40-70% of theory.

An example of an amino protective group $R_5$ which is stable under the reaction conditions is 9-fluorenylmethoxycarbonyl. An example of a carboxyl protective group $R_6$ which is stable under the reaction conditions is benzyl.

The carboxyl and/or amino protective groups which do not form part of the desired final product of the formula I are eliminated in a manner known per se, for example by solvolysis, in particular hydrolysis, alcoholysis or acidolysis, or by reduction, in particular hydrogenolysis or chemical reduction, where appropriate stepwise or simultaneously, it also being possible to use enzymatic methods.

In particular, a benzyl group $R_6$ can be eliminated by hydrogenation in the presence of a palladium on charcoal catalyst at room temperature, in which case 9-fluorenyl-methoxycarbonyl $R_5$ and the protective group $R_3$ are retained. 9-Fluorenyl-methoxycarbonyl $R_5$ can be eliminated as described in process a). The yields in the elimination of the protective groups are about 90-99% of theory.

The compounds of the formula I are preferably prepared by process b) and, especially, a).

Additional operations: Salts of compounds of the formula I with salt-forming groups can be prepared in a manner known per se. Thus, salts of compounds of the formula I with acid groups can be formed by reaction with a suitable base, for example by treatment with suitable metal compounds such as alkali metal salts of suitable organic carboxylic acids, for example the sodium salt of α-ethyl-caproic acid, or with suitable inorganic alkali metal or alkaline earth metal salts, in particular those derived from a weak and preferably volatile acid, for example sodium bicarbonate, or with ammonia or with a suitable organic amine, in which case stoichiometric amounts or only a small excess of the salt-forming agent are preferably used. Acid addition salts of compounds of the formula I are obtained in a customary manner, for example by treatment with an acid or with a suitable anion exchange reagent. Inner salts of compounds of the formula I which contain, for example, a free carboxyl group and a free amino group, can be formed, for example, by neutralization of salts, such as acid addition salts, to the isoelectric point, for example with weak bases, or by treatment with liquid ion exchangers. Salt formation takes place virtually quantitatively.

Salts can be converted virtually quantitatively into the free compounds in a customary manner, metal and ammonium salts for example by treatment with suitable acids, and acid addition salts for example by treatment with a suitable basic agent.

The reactive carboxylic acid derivatives of a compound of the formula I in which $R_2$ denotes hydrogen are prepared as is already described above for the detailed characterization of the reactive carboxylic acid derivatives. It is possible for this purpose, for example, to start from a compound of the formula I in which $R_1$ is an amino protective group, and $R_1$ denotes a suitable amino protective group and $R_2$ denotes hydrogen. The yields of reactive carboxylic acid derivative are about 85–98% of theory.

The processes described above, including the processes for the elimination of protective groups and the additional process measures, are, unless stated otherwise, carried out in a manner known per se, for example in the presence or absence of, preferably, inert solvents and diluents, if necessary, in the presence of condensing agents or catalysts, at reduced or elevated temperature, for example in a temperature range from about $-20°$ C. to about $150°$ C., in particular from about $0°$ C. to about $+70°$ C., preferably from about $+10°$ C. to about $+50°$ C., principally at room temperature, in a suitable vessel and, if necessary, in an inert gas, for example nitrogen, atmosphere.

This should entail the use, taking account of all the substituents present in the molecule, if necessary, for example in the presence of easily hydrolysable radicals, of especially mild reaction conditions such as short reaction times, use of mild acidic or basic agents in low concentration, stoichiometric ratios of amounts, choice of suitable catalysts, solvents, temperature and/or pressure conditions.

The invention also relates to those embodiments of the process which start from a compound obtainable as intermediate at any stage of the process, and the missing steps in the process are carried out, or in which the process is terminated at any stage, or a starting material is formed under the reaction conditions or is used in the form of a reactive derivative or salt. This preferably entails starting from those starting materials which lead in the process to the compounds described above as particularly valuable.

The invention also relates to the use of the compounds of the formula I, in particular the use of those compounds of the formula I in which $R_1$ denotes an amino protective group such as benzyloxycarbonyl, allyloxycarbonyl, tert.-butyloxycarbonyl or, in particular, 9-fluorenyl-methoxycarbonyl, $R_2$ denotes hydrogen and $R_3$ denotes 4-monomethoxytrityl, 4,4'-dimethoxytrityl or, in particular, triphenylmethyl (trityl), and to the use of the reactive carboxylic acid derivatives of these compounds for the synthesis of peptides, especially on solid phase, such as, for example, for Merrifield synthesis.

The invention also relates to substances which contain at least one bivalent radical of the formula VII in which n stands for 1 or 2, and $R_3$ denotes triphenylmethyl, 4-monomethoxy-trityl or 4,4'-dimethoxy-trityl, process for the preparation thereof and the use thereof for the synthesis of peptides. These substances are primarily peptide derivatives as are produced as intermediates, for example, in peptide synthesis. Accordingly, these peptide derivatives can also be bonded to a synthesis resin.

The Examples which follow illustrate the invention without restricting it. The temperatures are stated in degrees Celsius.

| Abbreviations | |
|---|---|
| But | = tert.-Butyl |
| Boc | = tert.-Butoxycarbonyl |
| Bzl | = Benzyl |
| Dhbt | = 3,4-Dihydro-3-hydroxy-4-oxo-1,2,3-benzotriazinyl |
| FAB-MS | = Fast atom bombardment mass spectrum |
| Fmoc | = 9-Fluorenyl-methoxycarbonyl |
| HPLC | = High-pressure liquid chromatography |
| conc. | = Concentrated |
| Pfp | = Pentafluorophenyl |
| Pmc | = 2,2,5,7,8-Pentamethyl-chroman-6-sulfonyl |
| m.p. | = Melting point |
| Tcp | = 2,4,5-Trichlorophenyl |
| THF | = Tetrahydrofuran |
| Tmob | = 2,4,6-Trimethoxy-benzyl |
| Trt | = Trityl (triphenyl-methyl) |
| Z | = Benzyloxycarbonyl |

EXAMPLE 1

Z-Asn(Trt)-OH

A mixture of 13.3 g of Z-Asn-OH (50 mmol), 26 g of triphenylmethanol (100 mmol), 150 ml of acetic acid and 9.5 ml (100 mmol) of acetic anhydride is stirred at 50° for 15 minutes. Addition of 0.25 ml of conc. sulfuric acid produces, after 5 minutes, a clear yellow solution. After 1½ hours, it is cooled and poured into 1.5 liters of ice-water. The precipitate is filtered off, thoroughly washed with water and dissolved in about 500 ml of ethyl acetate. The organic phase is washed with a saturated aqueous sodium chloride solution, dried over sodium sulfate and concentrated under reduced pressure to 250 g. Z-Asn(Trt)-OH is induced to crystallize by addition of 125 ml of hexane, m.p. 195°–196°.

EXAMPLE 2

H-Asn(Trt)-OH

A suspension of 10.2 g of Z-Asn(Trt)-OH (20 mmol) in 120 ml of one-normal aqueous hydrochloric acid is hydrogenated in the presence of 0.5 g of a 10% palladium on charcoal catalyst at room temperature and under atmospheric pressure. After uptake of hydrogen is complete, the catalyst is filtered off and thoroughly washed with methanol, and the filtrate is concentrated under reduced pressure to a weight of 100 g. Addition of 2.8 ml of triethylamine (20 mmol) is followed by further concentration to a weight of 50 g and the crystalline precipitate is filtered off and washed with a 1:1 mixture of methanol and water and then with water until free of chloride. The H-Asn(Trt)-OH contains 0.5 mole of water and slowly decomposes above 220°.

EXAMPLE 3

Fmoc-Asn(Trt)-OH 3.4 g of 9-fluorenylmethyl N-succinimidyl carbonate (10 mmol) are added and, at the same time, 1.4 ml of triethylamine are added dropwise so that the pH is 8.3–8.7 to a vigorously stirred solution of 3.8 g of H-Asn(Trt)-OH.0.5 H₂O (10 mmol) in 20 ml of tetrahydrofuran, 10 ml of water and 1.4 ml of triethylamine (10 mmol). After 20 minutes, the mixture is cooled in an ice bath and ethyl acetate and 25 ml of a one-molar aqueous potassium bisulfate solution are added. The organic phase is washed with water until free of sulfate, dried over sodium sulfate and concentrated under reduced pressure to about 50 g. The Fmoc-Asn(Trt)-OH can be

EXAMPLE 4

Fmoc-Asn(Trt)-OH

A suspension of 3.54 g of Fmoc-Asn-OH (10 mmol) and 5.2 g of triphenylmethanol (20 mmol) in 30 ml of acetic acid and 1.9 ml of acetic anhydride (20 mmol) is stirred at 50° for 15 minutes and then a solution of 0.05 ml of conc. sulfuric acid in 5 ml of acetic acid is added. After about one hour at 50° C. a solution forms, and after 1½ hours a precipitate starts to form. After 3 hours, 200 ml of ice-cold water are slowly added to the suspension, while cooling in ice, the mixture is briefly stirred, and the precipitate is filtered off and thoroughly washed with water. The moist material is dissolved in ethyl acetate, and the organic phase is washed with a saturated aqueous sodium chloride solution, dried over sodium sulfate and concentrated under reduced pressure. Before the product starts to crystallize out, the solution is diluted with 1,2-dichloroethane, concentrated again and filtered through 50 g of silica gel. The excess triphenylmethanol is eluted with 200 ml of 1,2-dichloroethane, and then Fmoc-Asn(Trt)-OH is eluted with 500 ml each of a 98:2 and of a 96:4 mixture, of 1,2-dichloroethane and methanol. The residue after evaporation to dryness is dissolved in 10 ml of tetrahydrofuran, 30 ml of ethyl acetate are added, the solution is concentrated to 20 g, and diisopropyl ether is added to crystallize; the Fmoc-Asn(Trt)-OH obtainable in this way melts at 210°–211° (with decomposition).

EXAMPLE 5

Fmoc-Asn(Trt)-OH

A solution of 0.69 g of Fmoc-Asn(Trt)-OBzl in 10 ml of a 9:1 mixture of methanol and water is hydrogenated in the presence of 0.07 g of a 10% palladium on charcoal catalyst at room temperature and under atmospheric pressure until starting material is no longer visible in the thin-layer chromatogram (solvent: 1:1 mixture of toluene and acetone). The filtrate after removal of the catalyst by filtration is evaporated, and the residue is dissolved in a 96:4 mixture of 1,2-dichloroethane and methanol and filtered through a little silica gel. Evaporation of the filtrate results in Fmoc-Asn(Trt)-OH, m.p. 210°–211° (with decomposition).

The starting material can be obtained as follows: Stage 5.1: 1.12 g of H-Asp-OBzl (5 mmol) and 1.05 g of sodium bicarbonate are suspended in 25 ml of a 9:1 mixture of dioxane and water, 1.85 g of solid 9-fluorenylmethyl N-succinimidyl carbonate are added, and the mixture is stirred at room temperature for 15 hours. The solution is concentrated and then diluted with ethyl acetate, the organic phase is washed with 0.5 molar aqueous potassium bisulfate solution and water and then dried over sodium sulfate and concentrated. Fmoc-Asp-OBzl crystallizes out after addition of petroleum ether.

Stage 5.2: 0.8 ml of 1-chloro-N,N,2-trimethyl-prop-1-enylamine (A. Devos et al., J. Chem. Soc., Chem. Commun., Vol. 1979, p. 1180) is added to a stirred solution of 2.09 g of Fmoc-Asp-OBzl in 20 ml of 1,2-dichloroethane at 0° under an argon atmosphere. After 10 minutes, a solution of 1.2 g of tritylamine in 4 ml of 1,2-dichloroethane is added, and then the mixture is stirred for 2 hours, diluted with ethyl acetate and washed with water. The organic phase is dried and evaporated. The residue is taken up in chloroform and chromatographed on 250 g of silica gel. The fractions containing the Fmoc-Asn(Trt)-OBzl are combined and evaporated; the product is obtained as an amorphous foam.

EXAMPLE 6

Z-Gln(Trt)-OH 1.1 ml of acetic anhydride (12 mmol) are added to a mixture of 2.8 g of Z-Gln-OH (10 mmol), 5.2 g of triphenylmethanol (20 mmol) in 30 ml of acetic acid, and the mixture is stirred at 50° for 15 minutes. Then 0.05 ml of conc. sulfuric acid (about 1 mmol) is added, resulting in a clear yellow solution after a few minutes. After 2 hours, the solution is added dropwise to 500 ml of water, while stirring and cooling in ice, and the precipitate is filtered off and thoroughly washed with water. The moist material is dissolved in ethyl acetate, the aqueous phase is separated off, and the organic phase is washed once with a saturated aqueous sodium chloride solution, dried over sodium sulfate and concentrated under reduced pressure to 20 g. Z-Gln(Trt)-OH is crystallized by addition of hexane in portions, m.p. 161°–162°.

EXAMPLE 7

H-Gln(Trt)-OH

A suspension of 10.4 g of Z-Gln(Trt)-OH (20 mmol) in 180 ml of a 9:1 mixture of methanol and water and 20 ml of one-normal aqueous hydrochloric acid is hydrogenated at room temperature and under atmospheric pressure in the presence of 0.5 g of a 10% palladium on charcoal catalyst; after the uptake of hydrogen is complete the starting material has dissolved. The catalyst is filtered off and washed with methanol; the filtrate is concentrated to 200 g and, at 60°, 2.8 ml of triethylamine (20 mmol) are added, whereupon the product immediately starts to crystallize. The mixture is concentrated to 100 g and left to stand at about 4° for some time, and the crystals are filtered off and washed with a mixture of methanol and water until free of chloride. The H-Gln(Trt)-OH obtainable in this way contains 0.5 mole of water and melts at 233° (with decomposition).

EXAMPLE 8

Fmoc-Gln(Trt)-OH 3.4 g of 9-fluorenylmethyl N-succinimidyl carbonate (10 mmol) are added and, at the same time, 1.4 ml of triethylamine are added dropwise so that the pH is about 8.5 to a vigorously stirred solution of 4 g of the hemihydrate of H-Gln(Trt)-OH (10 mmol) in 20 ml of tetrahydrofuran and 10 ml of one-normal aqueous sodium hydroxide solution. After 20 minutes, the mixture is cooled in an ice bath, covered with a layer of ethyl acetate and acidified to a pH of 2–2.5 with 25 ml of one-molar aqueous potassium bisulfate solution. The organic phase is washed with water until neutral, dried over sodium sulfate and concentrated under reduced pressure to 30 g. The product is induced to crystallize by addition of 35 ml of diisopropyl ether in portions. After prolonged standing in the cold, the crystalline material is filtered off and washed once in a 1:4 mixture of ethyl acetate and diisopropyl ether and three times with diisopropyl ether. The Fmoc-Gln(Trt)-OH still contains 0.5 mole of diisopropyl ether even after prolonged drying at 60° under high vacuum, m.p. above 125° (slow melting with loss of diisopropyl ether).

EXAMPLE 9

Fmoc-Gln(Trt)-OH

A mixture of 7.4 g of Fmoc-Gln-OH (20 mmol) and 10.4 g of triphenylmethanol (40 mmol) in 300 ml of acetic acid is stirred at 100° for 10 minutes. Addition of 0.1 ml of conc. sulfuric acid is followed by stirring at 100° for a further 15 minutes to produce a clear yellow solution. This is evaporated at 60° under reduced pressure, and the residue is then dried under reduced pressure for 10 minutes. The solid residue is dissolved in 60 ml of acetic acid at 60°, left at 60° for 20 minutes, then 2 ml of acetic anhydride (20 mmol) are added, and after 1 hour at 60°, the mixture is evaporated under reduced pressure. The oily residue is dried at 60° for 10 minutes, then dissolved in 100 ml of acetic acid and added dropwise to 500 ml of ice-cold water. The precipitate is filtered off, thoroughly washed with water and dissolved in ethyl acetate; the aqueous phase is separated off, and the organic phase is washed with a saturated aqueous sodium chloride solution. The organic solution is dried over sodium sulfate and then evaporated to dryness, and the residue is dissolved in 50 ml of 1,2-dichloroethane and applied to 100 g of silica gel; elution is with 1,2-dichloroethane and 1,2-dichloroethane containing 2%, then 4% methanol. The fractions containing Fmoc-Gln(Trt)-OH are evaporated under reduced pressure, and the product is crystallized from a mixture of ethyl acetate and diisopropyl ether, m.p. above 125°.

EXAMPLE 10

H-Gln-Gln-Gln-Gln-Gln-Ser-Leu-Gly-OH

The peptide is prepared twice by Merrifield solid-phase synthesis, using Fmoc-Gln-OH in one synthesis and Fmoc-Gln(Trt)-OH in the other.

The peptide molecule is built up by a Merrifield synthesis starting from 1 g of so-called Fmoc-Gly-p-benzyloxybenzyl ester-polystyrene resin (1% crosslinked) supplied by Novabiochem (Läufelfingen, Switzerland), in which the carboxyl group of the glycine whose amino group is protected by 9-fluorenyl-methoxycarbonyl (Fmoc) is esterified with 4-methoxy-benzyl alcohol, with the carbon atom of the methoxy group being linked with an aromatic ring of the polystyrene resin which is 1% crosslinked with divinylbenzene and simultaneously serves as support material. This entails use of an automatic peptide synthesis apparatus which is suitable for the alternate elimination of the amino protective groups, in the present case the Fmoc group, and for the coupling on of the N-Fmoc-protected amino acid compounds. This entails, in the first step, the Fmoc protective group in the Fmoc-Gly-p-benzyloxybenzyl ester-polystyrene resin being removed and Fmoc-Leu-OH being coupled to the H-Gly-p-benzyloxybenzyl ester-polystyrene resin obtained in this way, and then the further N-Fmoc-amino acids being coupled stepwise in the sequence Fmoc-Ser(But)-OH and then either Fmoc-Gln-OH, Fmoc-Gln-OH, Fmoc-Gln-OH, Fmoc-Gln-OH and Fmoc-Gln-OH, or Fmoc-Gln(Trt)-OH, Fmoc-Gln(Trt)-OH, Fmoc-Gln(Trt)-OH, Fmoc-Gln(Trt)-OH and Fmoc-Gln(Trt)-OH to the peptide/resin intermediate obtained in each instance. The individual stages are carried out in accordance with the following scheme, using about 10 ml of the washing liquids in each case and carrying out the individual operations at room temperature, unless stated otherwise, and with the reaction mixture being regularly shaken in each instance:

Starting from 1 g of the Fmoc-Gly/resin starting material described above (loading: 0.47 mmol/g), the following process steps are carried out, repeating each time for each stage:

1. single wash with isopropanol for 0.8 minutes;
2. three washes for 0.5 minutes each with dimethylacetamide which has been degassed under reduced pressure (dimethylamine-free);
3. five treatments for 1.7 minutes each with a 1:4 mixture of piperidine and dimethylacetamide (elimination of the Fmoc protective group);
4. single wash with isopropanol for 0.8 minutes;
5. three washes for 0.5 minutes each with dimethylacetamide which has been degassed under reduced pressure (dimethylamine-free);
6. single wash with isopropanol for 0.8 minutes;
7. three treatments for 1.7 minutes each with a 1:4 mixture of piperidine and dimethylacetamide (for complete elimination of the Fmoc protective group);
8. two washes for 0.5 minutes each with dimethylacetamide which has been degassed under reduced pressure (dimethylamine-free);
9. single wash with isopropanol for 0.8 minutes;
10. six washes for 0.5 minutes each with dimethylacetamide which has been degassed under reduced pressure (dimethylamine-free);
11. addition of the coupling reagent which has been made ready in the interim (which is obtained as follows: a mixture of 1.4 mmol of the particular Fmoc-L-amino acid, 1.4 mmol of 1-hydroxy-1H-benzotriazole and 1.55 mmol of diisopropylcarbodiimide in 4 ml of dimethylacetamide (dimethylamine-free) is left at room temperature for about 30 minutes and then used). The coupling reaction itself takes about 60 minutes at room temperature;
12. single acetylation with a 1:1:8 mixture of acetic anhydride, pyridine and dimethylacetamide (dimethylamine-free) for 5 minutes;
13. three washes for 0.5 minutes each with dimethylacetamide which has been degassed under reduced pressure (dimethylamine-free);
14. single wash with isopropanol for 0.8 minutes and
15. two washes for 0.5 minutes with dimethylacetamide which has been degassed under reduced pressure (dimethylamine-free).

After the final amino acid has been coupled on, the above treatment steps 1-10 are carried out once again for the purpose of eliminating the Fmoc group.

The yields for each of the last five coupling steps with Fmoc-Gln-OH or Fmoc-Gln(Trt)-OH are determined by means of the 1-(9-fluorenylmethyl)-piperidine formed as byproduct with each elimination of the Fmoc group. For this purpose, each of the combined filtrates from steps 3–10 are diluted to a defined volume and evaluated by UV photometry ($\lambda_{max}$=299.8 nm, $\epsilon$=7,800). The yields for the series with Fmoc-Gln-OH are 99%, 97%, 98%, 49% and 72%, and for that with Fmoc-Gln(Trt)-OH are 100%, 100%, 99%, 99% and 100%.

The peptide is eliminated from the resin by treatment with about 10 ml of a (90:5:5) mixture of trifluoroacetic acid, water and 1,2-ethanedithiol for 8 minutes; the reaction mixture is filtered, the filtrate is concentrated under reduced pressure, and the peptide is precipitated with a 1:1 mixture of diisopropyl ether and hexane and dried. The abovementioned treatment with trifluoroacetic acid/water/1,2-ethanedithiol itself results in partial elimination also of the trityl groups (where present) and the tert.-butyl group. This elimination is completed by heating the peptide precipitate in trifluoroacetic acid/water/1,2-ethanedithiol (90:5:5) at 30° C., for 30 minutes. The resulting crude products from the syntheses with and without trityl protective groups are investigated by HPLC (column: Nucleosil 5C18, 250×4.6 mm; mobile phase: A=0.1% trifluoroacetic acid in water; B=0.1% trifluoroacetic acid in acetonitrile. Gradient: 0 to 40% B in 30 minutes; flow rate: 1 ml/minute. Detection: 215 nm).

The desired title product has a retention time of 17.98 minutes. The HPLC profile of the crude product from the synthesis with trityl protection of the glutamine residues shows a signal (8%) at a retention time of 18.65 minutes in addition to the title product (92%). The HPLC profile of the crude product from the synthesis without trityl protection of the glutamine residues shows a signal (70%) with a retention time of 18.38 minutes in addition to the title product (only 30%).

EXAMPLE 11

H-Arg-Arg-Ser-Asn-Gln-Val-Ser-Gln-Asn-Tyr-Pro-Ile-Val-Gin-Asn-Ile-Gln-Gly-Arg-Arg-OH

The title peptide is prepared twice by the synthesis scheme described in Example 10, firstly with unprotected Fmoc-Asn-OH and Fmoc-Gln-OH and secondly with Fmoc-Asn(Trt)-OH and Fmoc-Gln(Trt)-OH. Starting from Fmoc-Arg(Pmc)-resin (Novabiochem), the following amino acids are successively condensed on: Fmoc-Arg(Pmc), Fmoc-Gly, Fmoc-Gln or Fmoc-Gln(Trt), Fmoc-Ile, Fmoc-Asn or Fmoc-Asn(Trt), Fmoc-Gln or Fmoc-Gln(Trt), Fmoc-Val, Fmoc-Ile, Fmoc-Pro, Fmoc-Tyr(But), Fmoc-Asn or Fmoc-Asn(Trt), Fmoc-Gln or Fmoc-Gln(Trt), Fmoc-Ser(-But), Fmoc-Val, Fmoc-Gln or Fmoc-Gln(Trt), Fmoc-Asn or Fmoc-Asn(Trt), Fmoc-Ser(But), Fmoc-Arg(Pmc) and Fmoc-Arg(Pmc).

Figure 1A:
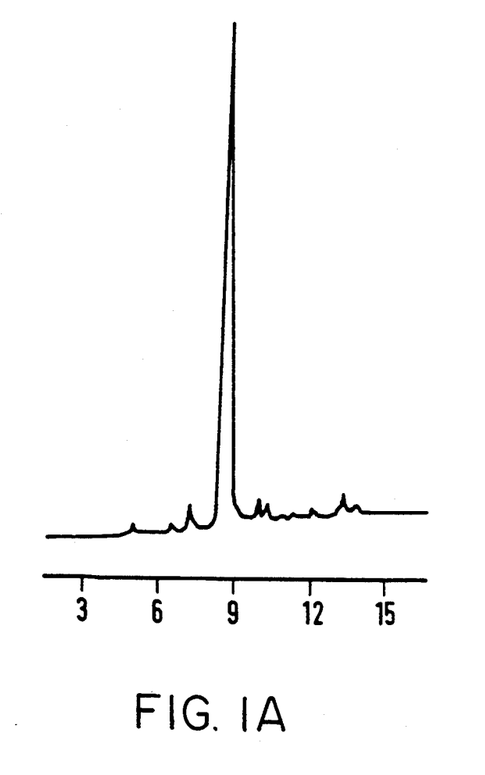
FIG. 1A is the high-pressure liquid chromatography profile of the following peptide, wherein Asn and Gln residues are protected by triphenylmethyl groups: H-Arg-Arg-Ser-Asn-Gln-Val-Ser-Gln-Asn-Tyr-Pro-Ile-Val-Gln-Asn-Ile-Gln-Gly-Arg-Arg-OH
Figure 1B:
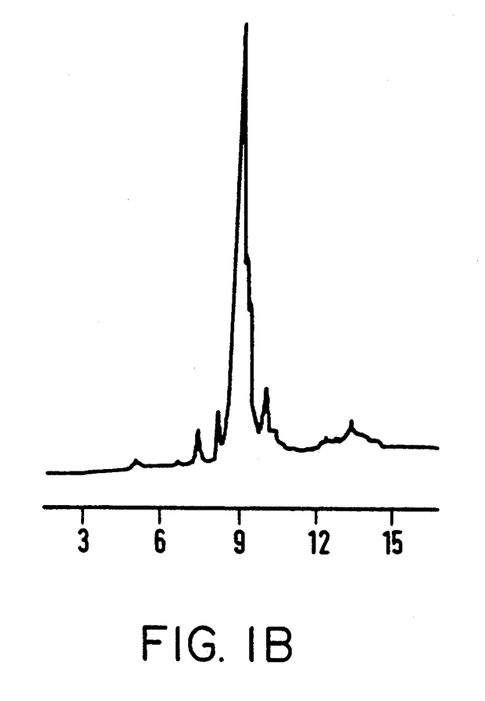
FIG. 1B is the high-pressure liquid chromatography profile of the same peptide, but lacking triphenylmethyl protection of Asn and Gln residues.

The peptide is eliminated from the resin after elimination of the N-terminal Fmoc group with trifluoroacetic acid/H$_2$O/1,2-ethanedithiol (90:5:5) for 8 minutes, and subsequently the remaining protective groups are removed with trifluoroacetic acid/H$_2$O/1,2-ethanedithiol/4-methylmercaptophenol (90:5:3:2) at 30° for 90 minutes. The crude product from synthesis a (with trityl protection) yields in the FAB-MS a $(M+H)^+$ signal at 2414.1 (calculated molecular weight: 2413.7). The HPLC profile (column: Nucleosil 7C18, 125×4.6 mm; mobile phase: A=0.1% trifluoroacetic acid in water, B=0.1% trifluoroacetic acid in acetonitrile. Gradient: 0 to 90% B in 30 minutes, 1.5 ml/minute. Detection: 215 nm) of the crude products from both syntheses (FIG. 1A with trityl protection for Asn and Gln; FIG. 1B: without trityl protection for Asn and Gln). The abscissa scale therein indicates the retention time in minutes.

EXAMPLE 12

Fmoc-Lys-Gln-His-Asn-Pro-Lys-Tyr-Gln-Trp-Asn-OH 3.35 ml (23.4 mmol) of 2,6-dichloro-benzoyl chloride (Fluka) are added in 4 portions within 5 hours to a suspension of 10 g of so-called 4-benzyloxybenzyl alcohol-polystyrene (0.78 mmol OH/g; 1% crosslinked with divinylbenzene; the phenyl groups of the polystyrene are substituted in the 4 position by 4-hydroxymethylphenyloxymethyl; Novabiochem), 9.3 g (15.6 mmol) of Fmoc-Asn(Trt)-OH and 3.1 ml (38.5 mmol) of pyridine in 60 ml of dimethylacetamide, and the mixture is stirred for 24 hours. The resin is filtered off and very thoroughly washed with methanol and 1,2-dichloroethane. The loading on the resin is 0.48 mmol/g (determination of Fmoc by photometry). The remaining OH groups are acetylated with acetic anhydride/pyridine/-dimethylacetamide 1:1:8 for 2 hours before the peptide synthesis starts. A Fmoc-Asn(Tmob)-resin is prepared in an analogous manner (replacement of Fmoc-Asn(Trt)-OH by Fmoc-Asn(Tmob)-OH). The latter has a loading of 0.44 mmol/g. 0.5 g of Fmoc-Asn(Trt)-resin (0.24 mmol of Asn) and 0.5 g of Fmoc-Asn(Tmob)-resin (0.22 mmol of Asn) are coupled successively with the following amino acids by the synthesis described in Example 10: Fmoc-Trp, Fmoc-Gln(Trt) or Fmoc-Gln(Tmob), Fmoc-Tyr(But), Fmoc-Lys(Boc), Fmoc-Pro, Fmoc-Asn(Trt) or Fmoc-Asn(Tmob), Fmoc-His(Trt), Fmoc-Gln(Trt) or Fmoc-Gln(Tmob), and Fmoc-Lys(Boc).

The resulting peptide-resins are shaken with trifluoroacetic acid/dimethyl sulfide/1,2-ethanedithiol (77:20:3) for 15 minutes in order to eliminate the peptide from the resin. The remaining protective groups are then eliminated with trifluoroacetic acid/water/1,2-ethanedithiol (90:5:5) at room temperature for 40 minutes.

The resulting crude products from the syntheses with trityl protection on Asn and Gln (=crude product A) on the one hand and with Tmob protection on Asn and Gln (=crude product B) on the other hand are investigated by HPLC (column: Nucleosil 5C18, 250×4.6 mm; mobile phase: A=0.1% trifluoroacetic acid in water; B=0.1% trifluoroacetic acid in acetonitrile. Gradient: 0 to 90% B in 30 minutes, 1 ml/minute. Detection: 215 nm). The desired title product has a retention time of 29.8 minutes. The HPLC profile of the crude product from the synthesis with trityl protection (crude product A) shows in addition to the title product (95%, $(M+H)^+$ in the FAB-MS=1565.4; calculated molecular weight: 1564.7) a signal (5%) at a retention time of 30.9 minutes for Fmoc—Lys—Gln—His—Asn—Pro—Lys—Tyr—Gln—Trp(CH$_2$—⟨phenyl⟩—OH)—Asn—OH.

The HPLC profile of crude product B (with Tmob protection) shows in addition to the signal for the title product (only about 8%) and the abovementioned signal (about 3%) with the retention time of 30.9 minutes, a signal (89%) with a retention time of 33.7 minutes for

[(M+H)+ in the FAB-MS=1745.6; calculated molecular weight: 1744.9] and other very small signals.

EXAMPLE 13

Fmoc-Asn(Trt)-OTcp

A solution of 1.5 g (2.51 mmol) of Fmoc-Asn(Trt)-OH and 0.54 g (2.75 mmol) of 2,4,5-trichloro-phenol in 10 ml of tetrahydrofuran is cooled to 0°. 0.57 g (2.75 mmol) of dicyclohexyl-carbodiimide in solid form is added, and the mixture is stirred at 0° for 30 minutes, at room temperature for 2 hours and again at 0° for 30 minutes, and then the dicyclohexylurea which has formed is filtered off. Fmoc-Asn(Trt)-OTcp is crystallized out of the filtrate by addition of 60 ml of hexane; m.p. 133°-135°, $[\alpha]_D^{20} = +51.1°$ (THF).

EXAMPLE 14

Fmoc-Gln(Trt)-OTcp 10 g (15.1 mmol) of Fmoc-Gln(Trt)-OH×0.5 diisopropyl ether and 3.26 g (16.6 mmol) of 2,4,5-trichlorophenol are dissolved in 100 ml of tetrahydrofuran and cooled to 0°. Addition of 3.41 g (16.6 mmol) of dicyclohexylcarbodiimide in solid form is followed by stirring at 0° for 1 hour, at room temperature for 2 hours and again at 0° for 30 minutes. The dicyclohexylurea which has crystallized out is filtered off, and Fmoc-Gln(Trt)-OTcp is precipitated as a gel from the filtrate by addition of 750 ml of petroleum ether and is filtered off, dried and crystallized from methylene chloride/hexane; m.p.=166°, $[\alpha]_D^{20} = -16.1°$ (THF).

EXAMPLE 15

Fmoc-Asn(Trt)-OPfp 1.5 g (2.51 mmol) of Fmoc-Asn(Trt)-OH are dissolved in 15 ml of tetrahydrofuran. 0.51 g (2.76 mmol) of pentafluoro-phenol is added, the solution is cooled to 0° and then 0.57 g (2.76 mmol) of dicyclohexyl-carbodiimide is also added in solid form. It is stirred at 0° for 30 minutes, at room temperature for 2 hours and again at 0° for 30 minutes. The dicyclohexylurea which has crystallized out is filtered off, and the filtrate is evaporated to dryness and triturated with 40 ml of diisopropyl ether. The powdery residue is filtered off, dried and recrystallized from methylene chloride/petroleum ether. Fmoc-Asn(Trt)-OPfp is obtained; m.p. 154°-156°, $[\alpha]_D^{20} = -7.8°$ (THF).

EXAMPLE 16

Fmoc-Gln(Trt)-OPfp 1.5 g (2.27 mmol) of Fmoc-Gln(Trt)-OH×0.5 diisopropyl ether and 0.46 g (2.5 mmol) of pentafluorophenol are dissolved in 35 ml of ethyl acetate, cooled to 0° and, while stirring, 0.52 g (2.5 mmol) of dicyclohexylcarbodiimide is added. The mixture is stirred at 0° for 1 hour and at room temperature for 3 hours, and insoluble material is filtered off and washed with tetrahydrofuran. The filtrate is evaporated to dryness, and the residue is dissolved in 30 ml of tetrahydrofuran. Slow addition of petroleum ether while stirring results in crystallization of Fmoc-Gln(Trt)-OPfp; m.p. 185°-187°, $[\alpha]_D^{20} = -16.4°$ (THF).

EXAMPLE 17

Fmoc-Asn(Trt)-ODhbt 1.5 g (2.51 mmol) of Fmoc-Asn(Trt)-OH are dissolved in 10 ml of tetrahydrofuran and mixed with a solution of 0.45 g (2.76 mmol) of 3,4-dihydro-3-hydroxy-4-oxo-1,2,3-benzotriazine in 5 ml of dimethylformamide. The mixture is cooled to 0°, and 0.57 g (2.76 mmol) of dicyclohexylcarbodiimide in solid form is added, and the mixture is stirred at 0° for 1 hour, at room temperature for 3 hours and then again at 0° for 1 hour. The dicyclohexylurea which has separated out is filtered off, the filtrate is evaporated to dryness, and the residue is triturated with 30 ml of diisopropyl ether, filtered off and dried. The crude product is purified by reprecipitation from methylene chloride/hexane. Fmoc-Asn(Trt)-ODhbt is obtained as an amorphous powder; m.p. about 140°, $[\alpha]_D^{20} = -40.8°$ (THF).

EXAMPLE 18

Fmoc-Gln(Trt)-ODhbt 1 g (1.51 mmol) of Fmoc-Gln(Trt)-OH×0.5 diisopropyl ether is dissolved in 10 ml of ethyl acetate. 0.27 g (1.66 mmol) of 3,4-dihydro-3-hydroxy-4-oxo-1,2,3-benzotriazine is added in finely powdered form and, after the suspension has been cooled to 0°, 0.34 g (1.66 mmol) of dicyclohexyl-carbodiimide is also added in solid form. After stirring at 0° for one hour, a further 10 ml of ethyl acetate is added, the mixture is stirred at room temperature for 3 hours, and the dicyclohexylurea is filtered off and washed with ethyl acetate. The filtrate is concentrated to about 10 ml and Fmoc-Gln(Trt)-ODhbt is crystallized from this by addition of 50 ml of petroleum ether; m.p. 130°-133°, $[\alpha]_D^{20} = -53.7°$ (THF).

EXAMPLE 19

H-Asn(Trt)-OH×0.5 H2O 20 g (0.1515 mole) of H-Asn-OH and 78.8 g (0.303 mole) of Trt-OH are suspended in 455 ml of glacial acetic acid. 9.28 ml (0.174 mole) of concentrated $H_2SO_4$ are added, followed by 28.6 ml (0.303 mole) of acetic anhydride, and the mixture is stirred at 60° for 75 minutes. Everything has dissolved after about 40–50 minutes. The reaction product is precipitated by slow introduction into 910 ml of ice-cold $H_2O$. The pH is then adjusted to about 6 with about 850 ml of 10N NaOH. Stirring at 0° for about 1 hour is followed by filtration, washing several times with $H_2O$ and then with toluene until the filtrate no longer contains Trt-OH. The resulting title product decomposes slowly above 220°.

EXAMPLE 20

Boc-Asn(Trt)-OH 3.83 g (10 mmol) of H-Asn(Trt)-OH×0.5 H$_2$O and 1.37 ml (10 mmol) triethylamine are dissolved in 38 ml of 90% strength tetrahydrofuran. 2.2 ml (10 mmol) of di-tert.-butyl dicarbonate are added, followed by a further 1.37 ml of triethylamine. Reaction is allowed to take place at room temperature for 2½ hours and then the mixture is extracted with 250 ml of ethyl acetate and 125 ml of aqueous one-molar KHSO$_4$ solution. The organic phase is washed until neutral, dried over Na$_2$SO$_4$ and evaporated to dryness. The residue is crystallized from methanol/ethyl acetate/hexane; m.p. of the resulting title product: 201°–203°, $[\alpha]_D^{20} = -17.7° \pm 1°$ (THF).

EXAMPLE 21

Boc-Gln(Trt)-OH 3.98 g (10 mmol) of H-Gln(Trt)-OH×0.5 H$_2$O and 1.38 ml (10 mmol) of triethylamine are suspended in 60 ml of 90% strength tetrahydrofuran, then 2.28 ml (10.2 mmol) of (Boc)$_2$O and a further 1.38 ml of triethylamine are added and the mixture is stirred at room temperature for 2 hours. A clear solution is produced after about 30 minutes. The subsequent procedure is in analogy to Example 20 with the difference that the residue is crystallized from methanol/CH$_2$Cl$_2$/petroleum ether; m.p. of the resulting title product: about 112°, $[\alpha]_D^{20} = -2° \pm 1°$ (THF).

We claim:

1. A compound of the formula I in which n stands for 1 or 2, R$_1$ denotes hydrogen or an amino protective group, R$_2$ denotes hydrogen or a carboxyl protective group and R$_3$ denotes triphenylmethyl, 4-monomethoxytrityl or 4,4'-dimethoxy-trityl, or a salt thereof when at least one of R$_1$ and R$_2$ is hydrogen, or a reactive carboxylic acid ester, anhydride, or cyclic amide thereof when R$_1$ is an amino protective group and R$_2$ is hydrogen.

2. A compound according to claim 1 of the formula I in which R$_1$ denotes an amino protective group, R$_2$ denotes hydrogen and R$_3$ denotes triphenylmethyl, 4-monomethoxy-trityl or 4,4'-dimethoxy-trityl, or a metal or ammonium salt thereof.

3. A compound according to claim 1 of the formula I in which R$_1$ denotes benzyloxycarbonyl, 9-fluorenyl-methoxycarbonyl, allyloxycarbonyl or tert.-butyloxycarbonyl, R$_2$ denotes hydrogen and R$_3$ denotes triphenylmethyl, or a metal or ammonium salt thereof.

4. A compound according to claim 1 of the formula I in which R$_1$ denotes 9-fluorenylmethoxycarbonyl, or a metal or ammonium salt of such a compound in which R$_2$ stands for hydrogen.

5. Benzyloxycarbonyl-Asn(triphenylmethyl)-OH or a metal or ammonium salt thereof according to claim 1.

6. 9-Fluorenyl-methoxycarbonyl-Asn(triphenylmethyl)-OH or a metal or ammonium salt thereof according to claim 1.

7. H-Asn(triphenylmethyl)-OH or a salt thereof according to claim 1.

8. Tert.-butyloxycarbonyl-Asn(triphenylmethyl)-OH or a salt thereof according to claim 1.

9. Benzyloxycarbonyl-Gln(triphenylmethyl)-OH or a metal or ammonium salt thereof according to claim 1.

10. 9-Fluorenyl-methoxycarbonyl-Gln(triphenylmethyl)-OH or a metal or ammonium salt thereof according to claim 1.

11. H-Gln(triphenylmethyl)-OH or a salt thereof according to claim 1.

12. Tert.-butyloxycarbonyl-Gln(triphenylmethyl)-OH or a salt thereof according to claim 1.

13. A reactive carboxylic acid ester, anhydride or cyclic amide according to claim 1 of a compound of formula I in which R$_1$ is an amino protective group and R$_2$ stands for hydrogen.

14. A reactive carboxylic acid ester or anhydride according to claim 13 in the form of a 2,4,5-trichlorophenyl ester, pentafluoro-phenyl ester, of an acid chloride, of a symmetric anhydride, of an ester with 1-hydroxybenzotriazole or of an ester with 3,4-dihydro-3-hydroxy-4-oxo-1,2,3-benzotriazine or of an ester with N-hydroxy-5-norbornene-2,3-dicarboximide.

15. 9-Fluorenyl-methoxycarbonyl-Asn(triphenylmethyl)-O-2,4,5-trichlorophenyl according to claim 1.

16. 9-Fluorenyl-methoxycarbonyl-Gln(triphenylmethyl)-O-2,4,5-trichlorophenyl according to claim 1.

17. 9-Fluorenyl-methoxycarbonyl-Asn(triphenylmethyl)-O-pentafluoro-phenyl according to claim 1.

18. 9-Fluorenyl-methoxycarbonyl-Gln(triphenylmethyl)-O-pentafluoro-phenyl according to claim 1.

19. 9-Fluorenyl-methoxycarbonyl-Asn(triphenylmethyl)-O-3,4-dihydro-3-hydroxy-4-oxo-1,2,3-benzotriazinyl according to claim 1.

20. 9-Fluorenyl-methoxycarbonyl-Gln(triphenylmethyl)-O-3,4-dihydro-3-hydroxy-4-oxo-1,2,3-benzotriazinyl according to claim 1.

* * * * *